United States Patent [19]

Venkateshwaran

[11] Patent Number: 5,762,953
[45] Date of Patent: Jun. 9, 1998

[54] TRANSDERMAL PROPENTOFYLLINE COMPOSITIONS FOR THE TREATMENT OF ALZHEIMERS DISEASE

[75] Inventor: Srinivasan Venkateshwaran, Salt Lake City, Utah

[73] Assignee: Theratech, Inc., Salt Lake City, Utah

[21] Appl. No.: 701,711

[22] Filed: Aug. 22, 1996

[51] Int. Cl.$^6$ .................................................. A61F 13/02
[52] U.S. Cl. ............................................ 424/448; 424/449
[58] Field of Search ...................................... 424/448, 449

[56] References Cited

U.S. PATENT DOCUMENTS

| | | | |
|---|---|---|---|
| 4,289,776 | 9/1981 | Mohler et al. | 424/253 |
| 4,719,212 | 1/1988 | Goto | 514/263 |
| 4,784,999 | 11/1988 | Angersbach | 514/263 |
| 5,446,070 | 8/1995 | Mantelle | 514/772.6 |
| 5,565,462 | 10/1996 | Eitan | 514/262 |

OTHER PUBLICATIONS

L.F.M. Scinto et al., Arch. Neurol. 51, 682 (1994).
L.L. Heston et al., Arch Gen. Psychiatry, 38, 1084 (1981).
B.A. Yankner, M.M. Mesulman, N. Eng. J. Med., 325, 1849 (1991).
R.D. Terry, R. Katzman, *The Neurology of Aging*, Eds., 51–84, Davis Philadelphia (1983).
D. A. Evans, J. Am. Med. Assoc., 262, 2551 (1989).
Saletu, et al. Nuropsychobiology, 24, 173 (1990–1991).
Moller, et al., Pharmacopsychiatry, 27, 159 (1994).
M. Nakashima et al., Basic Pharmacol. Ther., 14, 3219 (1989).
M. Nakashima et al., Basic Pharmacol. Ther., 14, 3241 (1989).
M. Nakashima et al., Basic Pharmacol. Ther., 14, 3255 (1989).

*Primary Examiner*—D. Gabrielle Phelan
*Attorney, Agent, or Firm*—Thorpe North & Western

[57] ABSTRACT

Patients suffering from Alzheimer's disease are treated by transdermally administering an effective amount of propentofylline in the form of an occulsive device containing a delivery composition comprising a carrier vehicle having uniformly distributed therein effective amounts of propentofylline and, optionally, a penetration enhancer. The occulsive device may be a matrix type patch in which the carrier vehicle is a pressure sensitive adhesive or a reservoir type patch in which the carrier vehicle is a liquid of controlled viscosity, i.e. a gel, wherein the reservoir system contains means for maintaining it in a propentofylline transferring relationship with the derma when applied. Daily dosages of between about 5 and 49 mg/day are sufficient to maintain adequate plasma propentofylline levels.

41 Claims, No Drawings

TRANSDERMAL PROPENTOFYLLINE COMPOSITIONS FOR THE TREATMENT OF ALZHEIMERS DISEASE

FIELD OF THE INVENTION

The present invention relates to a method for the delivery of a pharmaceutical agent for the treatment of memory disfunctions. More particularly, this invention relates to non-oral and noninvasive methods of delivery of a therapeutic agent used for the treatment of memory disfunctions. Specifically, this invention relates to a transdermal method of delivery of 1,2,3,6-tetrahydro-3-methyl-1-(3-oxohexyl)-7-propylpurine-2,6-dio ne (hereinafter referred to as propentofylline).

INTRODUCTION AND PRIOR ART

Various potential routes for the delivery of pharmaceutical agents have been considered: invasive (e.g. direct injection: intravenous, subcutaneous, intramuscular and depot systems) and non-invasive (e.g. pulmonary, oral, nasal, buccal, ocular, rectal, vaginal and transdermal). Administration of drugs by injection is not suitable for ambulatory patients and is not generally acceptable to patients undergoing drug therapy for chronic diseases. Also this route is far from being an ideal route of administration of molecules with short biological half-lives which necessitate repeated injections.

The oral delivery route is often proposed as being superior to all others. However, the delivery of some drugs using the oral route is fraught with difficulties which center around low bioavailability. Some of the factors responsible for low bioavailability are chemical and proteolytic degradation in the GI tract, low permeability of the absorbing tissues due to the size, hydrophilicity and charge characteristics of the drugs, and first pass metabolism in the liver. For drugs with short half-lives, multiple daily dosing would be required. Fluctuations in plasma concentrations due to a combination of low bioavailability and frequent dosing regimen cause wide fluctuations in plasma levels that can lead to pharmacological extremes ranging from drug (and metabolite) associated side effects to significant periods of therapeutically inadequate dosing.

The transdermal delivery of drugs overcomes a number of the disadvantages of the parenteral and oral route of administration. Aside from being a non-invasive route of administration, the generally recognized advantages of transdermal administration of a drug are avoidance of first-pass metabolism, better control of drug and metabolite plasma levels leading to improved therapy with reduced side effects, reduced frequency of dosing leading to improved patient compliance and convenience, especially in elderly and nursing home care situations.

Alzheimer's disease (AD) is a neurodegenerative disorder of the central nervous system leading to progressive dementia. The disease is characterized by progressive memory loss and the decline of other higher cognitive functions. L. F. M. Scinto et al., *Arch. Neurol.*, 51, 682 (1994); L. L. Heston et al., *Arch. Gen. Psychiatry*, 38, 1084 (1981); B. A. Yankner, M. M. Mesulman, *N. Eng. J. Med.*, 325, 1849 (1991); R. D. Terry, R. Katzman, *The Neurology of Aging*, Eds., 51–84, Davis, Philadelphia (1983). Approximately 1 out of 10 people of age 65 and over suffer from mild to moderate dementia. D. A. Evans, *J. Am. Med. Assoc.*, 262, 2551 (1989).

Drugs which stop the progression of dementia have not been developed; however, nootropics and metabolically active compounds such as vinca alkaloids and ergot alkaloids as well as alkylxanthines have been evaluated for symptomatic treatment of Alzheimer's disease. One such compound of particular interest is propentofylline, (1-(5'-oxohexyl)-3-methyl-7-propylxanthine), a nucleoside transport inhibitor with neuroprotective effects in cerebral ischemia which has been shown to positively influence clinical parameters in placebo controlled trials for the treatment of mild to moderate dementia. The neuroprotective effect of propentofylline, although not producing an acute improvement in the patient's condition, does cause a reduction in the rate of deterioration. Propentofylline is marketed in Japan for the treatment of emotional disturbance and as a vasodialator in the treatment of cerebral hemorrhage and cerebral arteriosclerosis.

Propentofylline has been employed in the treatment of Alzheimer's dementia with some success. U.S. Pat. No. 4,719,212 discloses several methods of administering propentofylline for the treatment of dementia. The proposed methods of administration are oral, rectal, intramuscular and intravenous. The clinical daily dosage for humans is stated to range from 50 or 100 to 1500 mg per day depending on the route of administration. These are administered in dosage units wherein dosage unit amounts are stated to be 50–800 mg for oral delivery, 100–1000 mg for rectal administration and 25–600 mg for injection administration.

Saletu, et al. *Neuropsychobiology*, 24, 173 (1990–91) and Moller, et al., *Pharmacopsychiatry*, 27, 159 (1994) reference the administration of propentofylline as 300 mg tablets t.i.d. (e.g. 900 mg/day), taken 1 hour before meals, in the treatment of mild to moderate dementia. Such multiple daily dosing regimens significantly reduce patient compliance in any patient suffering from AD, and especially in elderly patients, which in turn can adversely affect the overall management of AD in any stage of dementia.

Information on the pharmacokinetics of propentofylline and its metabolism in humans is available in scientific literature. M. Nakashima et al., *Basic Pharmacol. Ther.*, 14, 3219 (1989); M. Nakashima et al., *Basic Pharmacol. Ther.*, 14, 3241 (1989); M. Nakashima et al., *Basic Pharmacol. Ther.*, 14, 3255 (1989). It undergoes extensive hepatic first pass metabolism primarily to inactive metabolites. The absolute bioavailability after oral administration of propentofylline is on the order of 5–10%. Drug interactions with food further reduce bioavailability. The elimination half-life of propentofylline in humans is 15–45 minutes. Thus oscillations in plasma drug and metabolite concentrations due to multiple daily dosing regimens, variable first-pass metabolism and short half-lives can lead to pharmacological extremes ranging from drug and metabolite associated side effects to significant periods of therapeutically inadequate dosing. The most frequent side effects associated with oral propentofylline treatment are headaches, dizziness, gastrointestinal pain and nausea.

It can be concluded from the pharmacokinetic data in the literature that in the oral dosing regimen (300 mg t.i.d) used for the treatment of Alzheimer's dementia, the propentofylline plasma concentration in multiple daily dosing regimen should be the same as that following a single dose, with no steady state levels achieved. This is due to the very short half-life of the drug. Also the plasma propentofylline concentration 2 hours following a single 300 mg oral dose should be on the order 10 ng/ml. Assuming that a steady state plasma concentration of 10 ng/ml would be therapeutically effective in the treatment of Alzheimer's dementia, a transdermal input rate of 30 mg/day should be adequate to maintain this target propentofylline plasma concentration.

Thus, based on this assumption, the transdermal propentofylline daily dose for the treatment of Alzheimer's dementia is significantly lower than previously recognized as necessary for other non-parenteral routes of administration.

In addition to a significantly reduced dose, transdermal delivery of propentofylline also provides other significant advantages over the oral, rectal or injection method. A transdermal system avoids hepatic first-pass metabolism and thereby provides an increased amount of the active drug to the body systems; undesirable food interactions are also eliminated. The transdermal delivery of propentofylline provides constant, therapeutically effective blood levels, thereby promoting reduced side effects while maximizing the therapeutic benefits of the drug. Additionally, patient compliance and convenience would be significantly improved with a once a day transdermal dosing regimen versus multiple daily oral or other prior art dosing. Longer duration of transdermal dosing (up to once-a-week) may also be possible. Patient compliance is further enhanced because of the pain-free manner of drug administration as compared to the use of hypodermic needles or rectal insertion.

DESCRIPTION OF THE INVENTION

It is an object of the invention to provide a system and method for the transdermal delivery of propentofylline that provides significant advantages over prior art methods including avoidance of first-pass metabolism, better control of plasma drug and metabolite levels, lower overall dosing, improved patient convenience and compliance and which is less traumatic to the patient and care-giver.

Another object of the invention is to provide a method of noninvasively delivering effective amounts of propentofylline through the skin.

A further object of the invention is to provide a method of administration of propentofylline which provides for the desired concentration of the pharmaceutical agent in the patients blood stream at a constant level over a sustained period of time.

Another object of the invention is a method which provides for the maintenance of the desired concentration of propentofylline in the blood stream over time while utilizing a minimal daily and unit dosage amounts.

These and other objects may be realized by means of a composition for transdermal delivery consisting of propentophylline in an appropriately formulated occulsive adhesive device. The invention may optionally use effective amounts of enhancing components and propentophylline dissolved in, or admixed in a suitable carrier vehicle such as a member selected from the group consisting of a biocompatible pressure sensitive adhesive and a fluid, e.g. a suspension, emulsion or solution, of controlled viscosity. Suitable pressure sensitive adhesives will be subsequently described. Fluids of controlled viscosity include water, optionally containing a lower alkanol. Also, other inert ingredients which are soluble within the propentofylline/enhancer composition may be utilized in the place of water in forming fluids of any desired viscosity. Such fluids may be single phase, e.g. solutions, or phase separated systems such as suspensions or emulsions. The continuous phase forming such liquids can vary from hydrophilic to hydrophobic depending upon the desired combination. Representative inert ingredients other than water include, but are not limited to, a monoalcohol selected from the group consisting of ethanol, propanol, isopropanol and higher monoalcohols, propylene glycol, polypropylene glycol, polyethylene glycol, glycerol, polyvinyl alcohol, DMSO, dimethylformamide, 2-pyrrolidone; N-(2-hydroxyethyl) pyrrolidone, N-methylpyrrolidone, 1-dodecylazacycloheptan-2-one and other N-substituted-alkyl-azacycloalkyl-2-ones, petrolatum, polyvinylpyrrolidone, mineral oil, silicone oil, liquid sugars, waxes, petroleum jelly, ethylene-vinyl acetate polymers and mixtures thereof.

The propentofylline composition is preferably contained in an occlusive device for purposes of holding the composition against the skin surface for administration. Such devices are generally patches for adhesion to the skin surface and may be in either what is commonly referred to as a matrix or reservoir form.

A matrix patch is one where in the propentofylline/enhancer is admixed with a pressure sensitive adhesive to form a matrix. Matrix patches are formed by admixing the combination of propentofylline/enhancer and adhesive in a fluid or spreadable form. A uniform depth or thickness of admixture is spread or cast on a protective peelable release liner and a film backing is placed on the opposite side of the admixture to form a film sandwich with the propentofylline/enhancer/adhesive matrix in the center. The film sandwich is then die cut into the appropriate size and pouched in a protective pouch until ready for application. For use, the peelable release liner is removed and the propentofylline/enhancer/adhesive matrix is applied directly to the skin. The propentofylline and enhancer migrate from within the adhesive matrix to the skin surface. The enhancer functions to increase the flux of propentofylline through the skin.

In reservoir type patches, a carrier vehicle comprising a fluid of controlled viscosity, such as a gel or ointment, containing the propentofylline and optionally enhancer components is formulated for confinement in a reservoir having an impermeable backing and a skin contacting permeable membrane or membrane adhesive laminate providing diffusional contact between the reservoir contents and the skin. For application, the peelable release liner is removed and the patch is attached to the skin surface. The propentofylline/enhancer combination migrates from the gel or ointment across the membrane and adhesive, if present, and to the skin surface where the enhancer increases the permeation of the propentofylline through the skin. Preferably the reservoir type patches will be those having a peripheral adhesive ring for attachment to the skin surface such as are disclosed and claimed in U.S. Pat. Nos. 4,829,224 and 4,983,395, the disclosures of which are incorporated here by reference.

Also, the invention is drawn to treatment methods by means of which an effective amount of a propentofylline, optionally combined with the enhancer system, is applied to the skin of a human or animal subject for the treatment of Alzheimer's disease.

DETAILED DESCRIPTION OF THE PREFERRED EMBODIMENTS

The following definitions will be useful in describing the invention and will eliminate the need for repetitive explanations.

By "transdermal" delivery, the applicant intends the transdermal or percutaneous administration of propentophylline by passage of the drug through the skin as distinguished from the mucosal tissues.

When used in context, the terms "enhancement", "penetration enhancement" or "permeation enhancement" relates to an increase in the permeability of the skin, so as to increase the rate at which the propentofylline permeates through the skin layer. The enhanced permeation effected though the use of such enhancers can be observed, for example, by measuring the rate of diffusion of the drug through animal or human skin using a diffusion cell apparatus. The diffusion cell is described by Merritt et al. Diffusion Apparatus for Skin Penetration, *J. of Controlled Release*, 1 (1984) pp. 161–162.

By "application situs" is meant a site on the skin suitable for attachment of a reservoir delivery device, e.g., behind the ear, on the arm, back chest, stomach, leg, top of foot, etc.

"Carriers" or "vehicles" as used herein refer to carrier materials suitable for transdermal drug administration, and include any such materials known in the art, i.e., any liquid gel, solvent, liquid diluent, adhesive, or the like, which is nontoxic and which does not interact with other components of the composition in a deleterious manner. Carriers, which also may function as solvents in some instances, are used to provide the compositions of the invention in their preferred form. Examples of carriers for reservoir systems include, but not limited to, water, a monoalcohol selected from the group consisting of ethanol, propanol, isopropanol and higher monoalcohols, propylene glycol, polypropylene glycol, polyethylene glycol, glycerol, polyvinyl alcohol, DMSO, dimethylformamide, 2-pyrrolidone; N-(2-hydroxyethyl) pyrrolidone, N-methylpyrrolidone, 1-dodecylazacycloheptan-2-one and other N-substituted-alkyl-azacycloalkyl-2-ones, petrolatum, polyvinylpyrrolidone, mineral oil, silicone oil, liquid sugars, waxes, petroleum jelly, ethylene-vinyl acetate polymers and a variety of other oils and polymeric materials and mixtures thereof. Examples of carriers for matrix systems include adhesive materials such as polyacrylate, silicone, natural and synthetic rubbers or other adhesives.

By "effective" amount of a propentophylline is meant a nontoxic but sufficient amount of a compound to provide the desired therapeutic effect. An "effective" amount of permeation enhancer as used herein means an amount selected so as to provide the desired increase in skin permeability and, correspondingly, the desired depth of penetration, rate of administration and amount of propentofylline. By "effective amount of any enhancer or carrier component", e.g. lower alkanol or glycerin, is meant the amount found beneficial in a particular delivery system to achieve the desired delivery of the propentofylline from the system.

By "drug delivery system", "drug/enhancer composition" or any similar terminology is meant an occulusive device containing a formulated composition containing the propentofylline to be transdermally delivered in combination with such "carriers" or "vehicles", penetration enhancers, excipients, or any other additives.

By "occulsive device" or "occulsive adhesive device" is meant a matrix or reservoir system as defined herein.

By the term "matrix" or "matrix system" is meant propentofylline homogeneously combined in a biocompatible pressure sensitive adhesive which may or may not also contain other ingredients or in which the enhancer is also homogeneously dissolved or suspended. A matrix system is usually an adhesive patch having an impermeable film backing and, before transdermal application, a release liner on the surface of the adhesive opposite the film backing. A matrix system therefore is a unit dosage form of a propentofylline composition in an adhesive carrier, also containing the enhancer and other components which are formulated for maintaining the propentofylline composition in the adhesive in a drug transferring relationship with the derma, i.e. the skin.

By "fluid of controlled viscosity" is meant a vehicle or carrier in which propentophylline, enhancer and solvent when used, along with any other additives, are contained in a single or phase separated fluid state. The fluid per se may serve as a solvent or a solvent or co-solvent may be added. Such fluids can be water or organic based and may contain a mixture of liquids or solvents appropriately gelled or thickened. In other words, such fluids may comprise, but are not limited to, solutions, suspensions, emulsions, gels, ointments, creams, pastes or any other similar state which permits the outward diffusion of the propentophylline and enhancer and, optionally, a solvent or other additives as desired.

By the term "reservoir" or "reservoir system" is meant propentophylline combined in a fluid of controlled viscosity contained in an occlusive device having an impermeable back surface and an opposite surface configured appropriately with permeable membranes and adhesives for transdermal application. A reservoir system therefore is a unit dosage form of a drug composition in a fluid carrier of controlled viscosity, also containing the enhancer and other components which is formulated in an occlusive device for maintaining the propentofylline composition in the carrier in a drug transferring relationship with the derma, i.e. the skin.

The delivery compositions of this invention require, at a minimum, an effective amount of propentophylline permeant, a carrier vehicle comprising an adhesive or a fluid of controlled viscosity or gel and optionally an enhancer. Such fluids may be water based and contain a $C_2$ or $C_3$ alcohol with or without other optional ingredients within suitable ranges. However, solvents or liquids other than water may also be used as a base fluid phase. Preferred enhancers are cell envelope disordering compounds.

Cell envelope disordering compounds are known in the art as being useful in preparations for transdermal delivery devices. These compounds are thought to assist in skin penetration by disordering the lipid structure of the stratum corneum cell-envelopes. Comprehensive listings of exemplary compounds may be found in European Patent Application 43,738, published Jun. 13, 1982; U.S. Pat. Nos. 4,863,970; 4,888,354; 5,212,199 and 5,227,169 all of which are incorporated herein by reference as well as in subsequent patents and publications.

Certain of the cell envelope disordering compounds are generally encompassed by the formula:

R—X wherein R is a straight-chain alkyl of about 7 to 16 carbon atoms, a non-terminal alkenyl of about 7 to 22 carbon atoms, or a branched-chain alkyl of from about 13 to 22 carbon atoms, and X is —OH, —COOCH$_3$, —COOC$_2$CH$_5$, —OCOCH$_3$, —SOCH$_3$, —P(CH$_3$)2O, —COOC$_2$H$_4$OC2H$_4$OH, —COOCH(CHOH)$_4$CH$_2$OH, —COOCH$_2$CHOHCH$_3$, —COOCH$_2$CH(OR")CH$_2$OR", —(OCH$_2$CH$_2$)mOH, —COOR', or —CONR'$_2$ where R'is —H, —CH$_3$, —C$_2$H$_5$, —C$_3$H$_7$ or —C$_2$H$_4$OH; R"is —H, or a non-terminal alkenyl of about 7 to 22 carbon atoms; and m is 2–6; provided that when R" is an alkenyl and X is —OH or —COOH, at least one double bond is in the cis-configuration.

Other compounds such as sorbitan esters of $C_7$ to $C_{21}$ saturated and unsaturated alcohols are disclosed in U.S. Pat. Nos. 5,212,199 and 5,227,169.

Preferred cell-envelope disordering compounds are members selected from the group consisting of methyl laurate, lauryl alcohol, glycerol monolaurate, oleic acid, oleyl alcohol, glycerol monooleate, glycerol dioleate, glycerol trioleate, sorbitan monooleate, sorbitan monolaurate and lauramide diethanolamide and mixtures thereof. Preferred solvents are members selected from the group consisting of water and $C_2$ or $C_3$ alkanols and mixtures thereof.

U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol and an inert diluent such as water.

The composition may also contain other optional components which enhance their cosmetic appeal or acceptability, i.e., glycerin, thickeners, pigments, fragrances, perfumes, and the like. The penetration enhancing system is relatively free of skin irritation characteristics. Irritation, when present, is minor.

Glycerin is known in the industry as an emollient, such as taught by U.S. Pat. No. 4,687,481, and as an anti-irritant, as taught by U.S. Pat. No. 4,855,294.

Suitable thickening agents include hydrophilic polymers such as hydroxypropyl cellulose, hydroxypropyl methylcellulose, hydroxy ethylcellulose, ethylcellulose, carboxymethyl cellulose, dextran, gaur-gum, polyvinyl pyrrolidone, pectins, starches, gelatin, casein, acrylic acid, acrylic acid esters, acrylic acid copolymers, vinyl polymers, vinyl copolymers, vinyl alcohols, alkoxy polymers, polyethylene oxide polymers, polyethers, and the like.

Suitable pressure sensitive adhesives may include acrylic copolymer adhesives or "acrylic adhesive", (e.g. National Starch Durotak 80–1196 and Monsanto Gelva 737), rubber based adhesives or "rubber adhesive", such as polyisobutylene or "PIB adhesive", (e.g. Adhesive Research MA-24) and silicone based adhesives or "silicone adhesive", (e.g. Dow Bio-PSA). However, any other suitable pressure sensitive adhesives may also be used which are compatible with the propentofylline and enhancer when utilized.

Regardless of the type of system, i.e. reservoir or matrix, the concentration of propentofylline will generally vary between about 1 to 25 percent by weight of the overall delivery composition with ranges of between about 2 and 15 percent being preferred.

In a reservoir system the reminder of the composition is an enhancer/carrier combination. The carrier is preferably is made up of water and a lower alkanol, e.g. ethanol, propanol or isopropanol, mixture but may also include other solvents if desired. All ranges are in terms of the total propentofylline/carrier/enhancer composition. Preferably water will be present in amounts of between about 5 to 80 percent by weight with ranges of between about 15 to 40 percent being preferred. The alcohol may be present in amounts of between about 5 to 80 percent by weight with amounts of between about 10 to 50 percent being preferred. In addition to, or as a replacement for, water and alcohol, there may be used other solvents such as DMSO, N-methyl pyrrolidone, Azones, etc. When present, these will comprise from about 2.5 to 50 percent by weight of the composition with ranges of between about 2.5 and 20 percent being preferred.

The cell-envelope disordering type enhancer compounds which are used in combination with the solvent/carrier are present in amounts of between about 0.1 and 20 percent by weight with ranges of between about 0.2 and 10 percent being preferred.

Additionally, glycerin may be added as an anti-irritant or to modulate the delivery of the propentofylline and may be present in amounts of from 0 to 50 percent by weight. When used, glycerin is present in amounts of between about 5 and 50 percent with amounts of 10 to 50 percent being preferred.

For reservoir formulations water and ethanol or isopropanol are the preferred carriers.

In the matrix systems the carrier is primarily the pressure sensitive adhesive in which the propentofylline is homogeneously combined and which also contains a sufficient or effective amount of an enhancer such as the cell-envelope disordering compounds referenced above. As in the reservoir type system, the active propentophylline is present in amounts of between about 1 to 25 percent by weight with the 2 to 15 percent range being preferred. The adhesive is present in amounts ranging from 50 to 98 percent and will preferably be present in amounts of between about 70 and 96 percent. The enhancer is also homogeneously dissolved or suspended in the adhesive matrix and is present in amounts of between about 1 and 25 percent by weight with ranges of between about 2 to 15 percent being preferred.

In either event, the reservoir or matrix device is brought in contact with the skin at the application situs and is held in place on the skin at the application situs by a suitable adhesive. In the reservoir device, the drug enhancer composition may be applied to the skin through a permeable membrane forming the reservoir floor which is in diffusional contact with the skin.

As noted above, a steady state plasma concentration of propentofylline of about 10 ng/ml is considered to be therapeutically efficacious. A transdermal input rate of about 30 mg/day (1.25 mg/h) should be sufficient to maintain the 10 ng/ml plasma concentration. However, for purposes of this invention, target propentofylline ranges may vary from about 5 to 49 mg/day regardless of which type of transdermal delivery system is employed. To achieve the desired delivery rate, the size of the patch and the actual delivery area may vary. For reservoir type devices the overall patch size may range from about 10 to 100 cm$^2$ having an active delivery area of between about 3 to 50 cm$^2$. Such a system should deliver propentophylline through the skin at a rate of between about 0.001 to 1 mg/cm$^2$/hr. Preferably such devices will have an overall patch size ranging from about 15 to 60 cm$^2$ having an active delivery area of between about 5 to 30 cm$^2$. Such a system should deliver propentophylline through the skin at a rate of between about 0.02 to 0.7 mg/cm$^2$/hr. For matrix type devices the overall patch size may range from about 5 to 200 cm$^2$ having the same active delivery since the propentofylline is dispersed throughout the adhesive. Such a system should deliver propentophylline through the skin at a rate of between about 0.001 to 0.5 mg/cm$^2$/hr. Preferably such devices will have an overall patch size and delivery area ranging from about 10 to 100 cm$^2$. Such a system should deliver propentophylline through the skin at a rate of between about 0.004 to 0.2 mg/cm$^2$/hr.

It is to be understood that while the invention has been described in conjunction with the preferred specific embodiments thereof, that which follow are intended to illustrate and not limit the scope of the invention. Other aspects of the invention will be apparent to those skilled in the art to which the invention pertains.

EXAMPLES

The invention is more fully explained by the following examples without limiting the scope of the claim.

Example 1

Two reservoir type formulations (I and II) were prepared for the determination of initial propentofylline skin flux rates.

Approximately 4.0 ml of a base solution was prepared in a 7 ml glass vial. This solution consisted of 50% v/v of ethanol, USP; 15% v/v purified water (18 Mohm-cm); 30% v/v glycerin, USP; 1% v/v of glycerol monooleate (GMO, "Myverol® 18-99); 1% v/v methyl laurate (ML). To one solution was added sufficient propentofylline provide a concentration of about 72 mg/ml of solution (Formulation I) and to the other was added sufficient propentofylline to provide a concentration of about 131 mg/ml of solution (Formulation II). To each solution was added about 3% v/v of hydroxypropyl methylcellulose (Methocel® E10M) as a thickening agent. Table I shows the composition of each formulation.

TABLE I

Reservoir Patch Components

| Components | Formulation I | Formulation II |
|---|---|---|
| Propentofylline | 72 mg/ml | 131 mg/ml |
| Ethanol | 50% | 50% |
| Water | 15% | 15% |
| Glycerin | 30% | 30% |
| GMO | 1% | 1% |
| Methyl Laurate | 1% | 1% |
| Hydroxypropyl methylcellulose | 3% | 3% |

Each vial was then capped and gently rotated overnight to completely dissolve the gelling agent. The propentofylline concentration in Formulation I is approximately 7% w/v and in Formulation II is about 13% w/v. The resultant viscous gels (which would compare to the reservoir portion of a transdermal reservoir patch) were then used to conduct in vitro skin flux studies as follows.

Dermatomed (≈500 m thick) full thickness human cadaver skin was obtained from skin banks. The skin samples were packed in a foil pouch and shipped in dry ice. Upon receipt, the packages were thawed and the epidermal membrane was separated from the dermal layer following established methods. The epidermal membrane, consisting of intact stratum corneum and the epidermis, was blotted dry, wrapped in foil and stored at −5° C. until used. Information on age, race, sex and anatomical site of the donor skin was recorded when available.

In vivo skin flux studies were conducted using a heat separated human epidermal membrane and modified Franz diffusion cells. The epidermal membrane was cut into rectangular strips and mounted onto the diffusion cells between the donor and receiver compartments of a diffusion cell, with the epidermal side facing the receiver compartment, and clamped into place. The receiver compartment was then filled with purified water containing 0.02% sodium azide as a bacteriostat. In all cases, drug solubility in this receiver medium was adequate to ensure sink conditions throughout the experiment. The cell was then placed in a circulating water bath, calibrated to maintain the skin surface temperature at 32°±1° C. The skin was allowed to hydrate overnight under these conditions. The next day, 75 µl of a gelled formulation was pipetted into a cavity created by placing a polyethylene washer over the stratum corneum surface. This cavity was then occluded by clamping an occlusive backing film over it. At predetermined time points, the entire contents of the receiver compartment were collected for drug quantitation, and the receiver compartment refilled with fresh receptor medium, taking care to eliminate any air bubbles at the skin/solution interface. The cumulative amount of drug permeated per unit area at any time t($Q_t$, µg/cm²) was determined as follows:

$$Q_t = \sum_{n=0}^{t} (C_N * V)/A$$

where $C_n$ is the concentration (µg/ml) of the drug in the receiver sample for the corresponding sample time. V is the volume of fluid in the receiver chamber (~6.3 cm³), and A is the diffusional area of the cell (0.64 cm²). The slope of the best fit line to the $Q_t$ vs. t plot gives the steady state flux ($J_{ss}$, µg/cm²/hr); the intercept of this line on the time axis give the lag time ($t_L$,h).

Table II lists the cumulative amount of propentofylline (mg/cm²/24 h) delivered across six different donor skin samples.

TABLE II

| | Cumulative Amount (mean), mg/cm²/24h | |
|---|---|---|
| Donor No. | Formulation I | Formulation II |
| 1 | 2.33 | 3.85 |
| 2 | 1.74 | 1.68 |
| 3 | 2.86 | 3.67 |
| 4 | 2.08 | 2.14 |
| 5 | 0.79 | 1.06 |
| 6 | 1.66 | 2.16 |
| Mean | 1.97 | 2.31 |

The variability seen is typical of in vitro skin flux experiments and is primarily due to inter- and intra-donor variability.

Target flux specifications (expressed in mg/cm²/24 hr) depends upon the actual drug delivery surface area. For liquid reservoir patches, the actual drug delivery area is much less than the total patch size, because of the peripheral adhesive surrounding the reservoir. The target for these experiments is based on a 15 cm² active delivery area. Therefore, the target cumulative propentofylline delivery to achieve a 30 mg per day dose would be 2 mg/cm²/24 hr.

Formulation I delivered a flux which was very close to the target cumulative flux of 2.0 mg/cm²/24 hr. Formulation II, at nearly double the drug concentration of Formulation I, delivered an amount slightly higher (2.31 mg/cm²/24 hr) than the target amount which suggests that effective delivery of the active pronentofylline may be achieved using relatively low concentrations of active ingredient.

These data support the conclusion that transdermal delivery can provide a sustained 30 mg daily dosage at a constant migration rate of about 2 mg/cm²/24 h in a 15 cm² patch. Based on these data it is feasible to trandsermally administer a target range dosage of 5 to 49 mg/day of propentofylline. Further increase in delivery rate may also be possible with formulation optimization.

To illustrate that similar results can be obtained using a matrix type of system the following formulation was prepared.

Example II

Matrix laminates containing propentofylline (PF, Chemagis Ltd., Tel Aviv, Israel), an adhesive and an enhancer having the composition as given in Table III were fabricated as follows.

The percent solid adhesive of TSR adhesive (an acrylic copolymer adhesive of 2-ethyl hexyl acrylate (2-EHA) and N-vinyl pyrrolidone (NVP), Sekisui Chemical Co., Japan), was determined by weighing a small amount of adhesive solution in a preweighed aluminum dish. The solvent was evaporated by overnight drying in a convection oven at 70° C., and the dish was reweighed. The percent solids was calculated by dividing the dry weight by the wet weight and multiplying by 100. Known amounts of TSR adhesive solution were weighed into glass bottles. From the weight of the adhesive solution and the percent solid adhesive, the amount of adhesive in the solution was calculated. Appropriate quantities of propentofylline (PF) and optionally, a penetration enhancer selected from the group consisting of sorbitan monooleate (Arlacel 80, ICI Americas, Wilmington, Del.); sorbitan monolaurate (Arlacel 20, ICI Americas, Wilmington, Del.) or lauramide diethanolamide (Alkamide LE, Rhone-Poulenc, Cranbury, N.J.) were added to yield various compositions as shown in Table III (Formulations III–VIII), all percentages being calculated on a dry weight basis.

TABLE III

COMPOSITION OF FORMULATIONS EVALUATED

| | Formulation ID | | | | |
|---|---|---|---|---|---|
| Test Formulations | TSR Adhesive % w/w | PF % w/w | Alkamide LE % w/w | Arlacel 80 % w/w | Arlacel 20 % w/w |
| III | 80 | 10 | 0 | 10 | 0 |
| IV | 80 | 10 | 0 | 0 | 10 |
| V | 80 | 10 | 0 | 5 | 5 |
| VI | 90 | 10 | 0 | 0 | 0 |
| VII | 80 | 20 | 0 | 0 | 0 |
| VIII | 75 | 20 | 5 | 0 | 0 |

Each glass bottle was then tightly capped, sealed with laboratory film (PARAFILM "M", American National Can Company, Greenwich, Conn.), and rotated overnight until all ingredients had completely dissolved and the solution was clear.

About 8 ml of each of the drug/optional enhancer/TSR solutions represented by Formulas III–VIII was then dispensed on a release liner (siliconized polyester release liner, Release Technologies, Inc., W. Chicago, Ill.), and cast with a 10 mil gap casting knife. This cast mixture was dried in a convection oven at 70° C. for 15 minutes to yield a dry film approximately 2.0 mil thick. A backing film (polyethylene backing film, 3M Corp., St. Paul, Minn.) was then laminated onto the dry adhesive film using a rubber roller. This matrix laminate was used for in vitro skin flux measurements which were performed as described in the following paragraphs which closely parallel those of Example 1.

In vitro skin flux studies were conducted using modified Franz diffusion cells. Heat separated human epidermal membrane was cut into rectangular strips. The Formula III to VIII matrix laminates (described above) were cut into circular punches of 0.71 $cm^2$ surface area. After the release liner was peeled and discarded, the circular punches were laminated onto the stratum corneum surface of the epidermal membrane. Each piece of the skin-punched matrix sandwich was loaded between the donor and receiver compartments of a diffusion cell, with the epidermal side facing the receiver compartment, and clamped in place. The receiver compartment was then filled with 0.02% sodium azide solution and the cell was then placed in a circulating water bath calibrated to maintain the skin surface temperature at 32 ±1° C. At predetermined intervals, the entire contents of the receiver compartment was collected for drug quantitation, and the receiver compartment was refilled with fresh receptor medium, taking care to eliminate any air bubbles at the skin/solution interface. The cumulative amount of drug permeated per unit area at any time $t(Q_t, \mu g/cm^2)$ was determined as follows:

$$Q_t = \sum_{n=0}^{t} (C_N * V)/A$$

where $C_n$ is the concentration (µg/ml) of the drug in the receiver sample for the corresponding sample time, V is the volume of fluid in the receiver chamber (6.3 cm³), and A is the diffusional area of the cell (0.64 cm²). The mean amount of propentofylline (PF) permeated per cm² in 24 hr from each formulation is summarized in Table IV.

TABLE IV

CUMULATIVE 24 HOUR PF PERMEATION (Q24 – µg/cm²/24 hr)

| | Formulation ID | |
|---|---|---|
| Test Formulations | # of skin/cells | Q24– µmg/cm²/24 hr |
| III | 3/12 | 285.7 |
| IV | 3/12 | 295.4 |
| V | 3/12 | 284.2 |
| VI | 3/12 | 246.1 |
| VII | 3/12 | 322.9 |
| VIII | 3/12 | 472.2 |

The data shows that it is feasible to delivery PF across human skin from a transdermal matrix patch. These data show a delivery comparable to about 0.24 to 0.47 mg/cm²/day which is within the targeted range.

The compositions and in vitro transdermal delivery illustrated herein demonstrates that effective amounts of propentophylline can be delivered to a patient using a daily dosage of not more than 49 mg/day which is considerably less than that required by prior art methods.

The above examples are but illustrative of reservoir and matrix type of transdermal components which may be employed in the transdermal delivery of propentophylline. The invention is directed to the transdermal delivery of propentophylline and not to any specific reservoir or matrix type formulation. There are many components disclosed in the prior art for these type of formulations which may be functional in the present invention. Therefore, specific enhancers, solvents, adhesives, glycerin, of other components are not critical as long as they are compatible with propentophylline. Within the guidelines presented herein, a certain amount of experimentation to obtain optimal formulations can be readily carried out by those skilled in the art without departing from the invention which is limited in scope only by the following claims and functional equivalents thereof.

I claim:

1. A system for the transdermal delivery of propentofylline at a flux of between 0.001 and 1.0 mg/cm²/hr comprising an occlusive device having a diffusional surface area to provide a daily propentofylline dose at said flux of between 5 and 49 mg/day containing:

a delivery composition comprising a carrier vehicle having uniformly distributed therein effective amounts of propentofylline and, optionally, a penetration enhancer.

2. The system of claim 1 wherein the propentofylline comprises about 1 to about 25% by weight of the delivery composition.

3. The system of claim 2 wherein the occlusive device is a matrix system having a diffusional area of between about 5 and 200 cm² providing a propentofylline flux of 0.001 and 0.5 mg/cm²/hr wherein the carrier vehicle is a pressure sensitive adhesive which also serves as a means for maintaining the system in a propentofylline transferring relationship with the derma when applied.

4. The system of claim 3 containing an enhancer wherein the propentofylline and enhancer portion of said delivery composition are intimately admixed with said adhesive carrier vehicle.

5. The system of claim 4 wherein the delivery composition comprises between about 50 to 98 percent by weight of a pressure sensitive adhesive, 1 to 25 percent by weight of an enhancer and 1 to 25 percent by weight of propentofylline.

6. The system of claim 5 wherein the enhancer is a member selected from the group consisting of methyl laurate, lauryl alcohol, glycerol monolaurate, oleic acid, oleyl alcohol, glycerol monooleate, glycerol dioleate, glycerol trioleate, sorbitan monooleate, sorbitan monolaurate and lauramide diethanolamide and mixtures thereof.

7. The system of claim 6 wherein the pressure-sensitive adhesive carrier vehicle is a member selected from the group consisting of acrylic, rubber, and silicone adhesives.

8. The system of claim 7 wherein the pressure sensitive adhesive is present in amounts of between about 70 and 96 percent by weight.

9. The system of claim 8 wherein the enhancer is present in amounts of between about 2 and 15 percent by weight.

10. The system of claim 9 wherein the propentofylline is present in amounts of between about 2 and 15 percent by weight.

11. The system of claim 2 wherein the occlusive device is a reservoir system having a diffusional area of between about 3 and 50 cm² providing a propentofylline flux of 0.001 and 1.0 mg/cm²/hr wherein the carrier vehicle wherein the carrier vehicle is a fluid of controlled viscosity and which also contains means for maintaining the system in a propentofylline transferring relationship with the derma when applied.

12. The system of claim 11 wherein the fluid of controlled viscosity comprises a member selected from the group consisting of water, a monoalcohol selected from the group consisting of ethanol, propanol, isopropanol, and higher monoalcohols, propylene glycol, polypropylene glycol, polyethylene glycol, glycerol, polyvinyl alcohol, DMSO, dimethylformamide, 2-pyrrolidone; N-(2-hydroxyethyl) pyrrolidone, N-methylpyrrolidone, 1-dodecylazacycloheptan-2-one and other N-substituted-alkyl-azacycloalkyl-2-ones, petrolatum, polyvinylpyrrolidone, mineral oil, silicone oil, liquid sugars, waxes, petroleum jelly, ethylene-vinyl acetate polymers and mixtures thereof.

13. The system of claim 12 containing an enhancer wherein the propentofylline and enhancer portion of said delivery composition are intimately admixed with said fluid of controlled viscosity.

14. The system of claim 13 wherein the fluid of controlled viscosity comprises a mixture of water and a lower alkanol member selected from the group consisting of ethanol, propanol and isopropanol and a thickening agent.

15. The system of claim 14 wherein the delivery composition comprises between about 5 to 50 percent by weight water 5 to 60 percent by weight of a lower alkanol, 0.1 to 20 percent by weight of an enhancer and 1 to 25 percent by weight of propentofylline.

16. The system of claim 15 wherein the enhancer is a member selected from the group consisting of methyl laurate, lauryl alcohol, glycerol monolaurate, oleic acid, oleyl alcohol, glycerol monooleate, glycerol dioleate, glycerol trioleate, sorbitan monooleate, sorbitan monolaurate and lauramide diethanolamide and mixtures thereof.

17. The system of claim 16 which additionally contains between about 5 and 50% by weight of glycerin.

18. The system of claim 17 wherein said lower alkanol is ethanol.

19. The system of claim 18 wherein said delivery composition comprises 10 to 40 percent water, 10 to 50 percent water, 0.2 to 10 percent enhancer and 10 to 50 percent glycerin.

20. The system of claim 19 wherein said delivery composition contains 2 to 15 percent propentofylline.

21. A method for the treatment of Alzheimer's disease which comprises transdermally administering to a patient a daily dose of between 5 and 49 mg of propentofylline said dose being transdermally and continuously administered from an occlusive device adhering to the derma of a patient said device having a diffusional area sufficient to deliver propentofylline to said patient at a flux of between about 0.001 to 1 mg/cm²/hr from said device.

22. The method of claim 21 wherein said occlusive device adhering to the derma of a patient contains:

a delivery composition comprising a carrier vehicle having uniformly distributed therein effective amounts of propentofylline and, optionally, a penetration enhancer.

23. The method of claim 22 wherein the propentofylline comprises about 1 to about 25% by weight of the delivery composition.

24. The method of claim 23 wherein the occlusive device is a matrix system having a diffusional area of between about 5 and 200 cm² providing a propentofylline flux of 0.001 and 0.5 mg/cm²/hr wherein the carrier vehicle is a pressure sensitive adhesive which also serves as a means for maintaining the system in a propentofylline transferring relationship with the derma when applied.

25. The method of claim 24 wherein the delivery composition contains an enhancer and the propentofylline and enhancer portion of said delivery composition are intimately admixed with said adhesive carrier vehicle.

26. The method of claim 25 wherein the delivery composition comprises between about 50 to 98 percent by weight of a pressure sensitive adhesive, 1 to 25 percent by weight of an enhancer and 1 to 25 percent by weight of propentofylline.

27. The method of claim 26 wherein the enhancer is a member selected from the group consisting of methyl laurate, lauryl alcohol, glycerol monolaurate, oleic acid, oleyl alcohol, glycerol monooleate, glycerol dioleate, glycerol trioleate, sorbitan monooleate, sorbitan monolaurate and lauramide diethanolamide and mixtures thereof.

28. The method of claim 27 wherein the pressure-sensitive adhesive carrier vehicle is a member selected from the group consisting of acrylic, rubber, and silicone adhesives.

29. The method of claim 27 wherein the pressure sensitive adhesive is present in amounts of between about 70 and 96 percent by weight.

30. The method of claim 29 wherein the enhancer is present in amounts of between about 2 and 15 percent by weight.

31. The method of claim 30 wherein the propentofylline is present in amounts of between about 2 and 15 percent by weight.

32. The method of claim 23 wherein the occlusive device is a reservoir system having a diffusional area of between about 3 and 50 cm² providing a propentofylline flux of 0.001 and 1.0 mg/cm²/hr wherein the carrier vehicle is a fluid of controlled viscosity and wherein said system further contains means for maintaining the system in a propentofylline transferring relationship with the derma when applied.

33. The method of claim 32 wherein the fluid of controlled viscosity comprises a member selected from the group consisting of water, a monoalcohol selected from the group consisting of ethanol, propanol, isopropanol, and higher monoalcohols, propylene glycol, polypropylene glycol, polyethylene glycol, glycerol, polyvinyl alcohol, DMSO, dimethylformamide, 2-pyrrolidone; N-(2-hydroxyethyl) pyrrolidone, N-methylpyrrolidone, 1-dodecylazacycloheptan-2-one and other N-substituted-alkyl-azacycloalkyl-2-ones, petrolatum, polyvinylpyrrolidone, mineral oil, silicone oil, liquid sugars, waxes, petroleum jelly, ethylene-vinyl acetate polymers and mixtures thereof.

34. The method of claim 33 wherein the delivery composition contains an enhancer and the propentofylline and enhancer portion of said delivery composition are intimately admixed with said fluid of controlled viscosity.

35. The method of claim 34 wherein the fluid of controlled viscosity comprises a mixture of water and a lower alkanol member selected from the group consisting of ethanol, propanol and isopropanol and a thickening agent.

36. The method system of claim 35 wherein the delivery composition comprises between about 5 to 50 percent by weight water 5 to 60 percent by weight of a lower alkanol, 0.1 to 20 percent by weight of an enhancer and 1 to 25 percent by weight of propentofylline.

37. The method of claim 36 wherein the enhancer is a member selected from the group consisting of methyl laurate, lauryl alcohol, glycerol monolaurate, oleic acid, oleyl alcohol, glycerol monooleate, glycerol dioleate, glycerol trioleate, sorbitan monooleate, sorbitan monolaurate and lauramide diethanolamide and mixtures thereof.

38. The method of claim 37 wherein the delivery system additionally contains between about 5 and 50% by weight of glycerin.

39. The method of claim 38 wherein said lower alkanol is ethanol.

40. The method of claim 39 wherein said delivery composition comprises 10 to 40 percent water, 10 to 50 percent water, 0.2 to 10 percent enhancer and 10 to 50 percent glycerin.

41. The method of claim 40 wherein said delivery composition contains 2 to 15 percent propentofylline.

* * * * *

UNITED STATES PATENT AND TRADEMARK OFFICE
CERTIFICATE OF CORRECTION

PATENT NO : 5,762,953
DATED : June 9, 1998
INVENTOR(S) : S. Venkateshwaran

It is certified that error appears in the above-identified patent and that said Letters Patent is hereby corrected as shown below:

Col. 7, line 41, "reminder" should be replaced with --remainder--,
Col. 9, line 34, "500 m" should be replaced with --500 µm--,
Col. 14, line 10, "water" should be replaced with --lower alkanol--,
Col. 16, line 20, "water" should be replaced with --lower alkanol--.

Signed and Sealed this

Eighteenth Day of May, 1999

Attest:

Q. TODD DICKINSON

Attesting Officer    Acting Commissioner of Patents and Trademarks